United States Patent
Pan et al.

(10) Patent No.: US 6,436,629 B1
(45) Date of Patent: Aug. 20, 2002

(54) MODULATING ANGIOGENESIS

(75) Inventors: Duojia Pan, Dallas, TX (US); Gerald M. Rubin, Berkeley; Hongbing Zhang, El Cerrito, both of CA (US)

(73) Assignee: The Regents of the University of California, Oakland, CA (US)

( * ) Notice: Subject to any disclaimer, the term of this patent is extended or adjusted under 35 U.S.C. 154(b) by 19 days.

(21) Appl. No.: 09/697,854

(22) Filed: Oct. 27, 2000

(51) Int. Cl.⁷ .............................. C12Q 1/00; C12N 5/00; A61K 49/00
(52) U.S. Cl. .............................. 435/4; 435/375; 424/9.1; 424/9.2
(58) Field of Search ...................... 435/4, 375; 424/9.1, 424/9.2

(56) References Cited

FOREIGN PATENT DOCUMENTS

WO    WO 98/08933    *   3/1998

* cited by examiner

Primary Examiner—Anthony C. Caputa
Assistant Examiner—Gary B. Nickol
(74) Attorney, Agent, or Firm—Richard Aron Osman

(57) ABSTRACT

The invention provides methods and compositions relating to Kuz involvement in angiogenesis. In various embodiments, the invention provides methods for modulating angiogenesis by specifically modulating the activity of Kuz in a vertebrate animal predetermined to have a pathogenic angiogenesis; methods for modulating angiogenesis by specifically modulating the activity of Kuz in a vertebrate animal and subsequently detecting a resultant angiogenic modulation in the animal; methods for specifically detecting Kuz activity in a vertebrate animal predetermined to have a pathogenic angiogenesis; methods for specifically detecting a pathogenic angiogenesis in a vertebrate animal having a predetermined Kuz activity; and methods for identifying a modulator of angiogenesis by (a) contacting an angiogenic assay system comprising a predetermined amount of Kuz with a candidate agent, under conditions whereby but for the presence of the agent, the system provides a reference angiogenesis; and (b) detecting an agent-biased angiogenesis of the system.

8 Claims, No Drawings

MODULATING ANGIOGENESIS

FIELD OF THE INVENTION

The field of the invention is modulating angiogenesis by targeting a protein known as Kuz.

BACKGROUND OF THE INVENTION

Genes of the ADAM family encode transmembrane proteins containing both metalloprotease and disintegrin domains (reviewed in Black and White, 1998 Curr.Opin.Cell Biol. 10, 654–659; Wolfsberg and White, 1996 Dev.Biol. 180, 389–401), and are involved in diverse biological processes in mammals such as fertilization (Cho et al., 1998 Science 281, 1857–1859), myoblast fusion (Yagami-Hiromasa et al., 1995 Nature 377, 652–656) and ectodomain shedding (Moss et al., 1997 Nature 385, 733–736; Black et al., 1997 Nature 385, 729–733; Peschon et al., 1998 Science 282, 1281–1284). The Drosophila kuzbanian (kuz) gene represents the first ADAM family member identified in invertebrates (Rooke et al., 1996 Science 273, 1227–1231). Previous genetic studies showed that kuz is required for lateral inhibition and axonal outgrowth during Drosophila neural development (Rooke et al., 1996; Fambrough et al., 1996 PNAS.USA 93, 13233–13238.; Pan and Rubin, 1997 Cell 90, 271–280; Sotillos et al., 1997 Development 124, 4769–4779). Specifically, during the lateral inhibition process, kuz acts upstream of Notch (Pan and Rubin, 1997; Sotillos et al., 1997), which encodes the transmembrane receptor for the lateral inhibition signal encoded by the Delta gene. More recently, a homolog of kuz was identified in *C. elegans* (SUP-17) that modulates the activity of a *C. elegans* homolog of Notch in a similar manner (Wen et al., 1997 Development 124, 4759–4767).

Vertebrate homologs of kuz have been isolated in Xenopus, bovine, mouse, rat and human. The bovine homolog of KUZ (also called MADM or ADAM 10) was initially isolated serendipitously based on its in vitro proteolytic activity on myelin basic protein, a cytolasmic protein that is unlikely the physiological substrate for the bovine KUZ protease (Howard et al., 1996 Biochem.J. 317, 45–50). In a recent study, we showed that expression of a dominant negative form of the murine kuz homolog (mkuz) in Xenopus leads to the generation of extra neurons, suggesting an evolutionarily conserved role for mkuz in regulating Notch signaling in vertebrate neurogenesis (Pan and Rubin, 1997). We have now generated mkuz-deficient mice using gene targeting in embryonic stem (ES) cells. We show that mkuz is essential for embryonic development. mkuz mutant mice die around embryonic day (E) 9.5, with severe defects in the nervous system, the paraxial mesoderm and the yolk sac vasculature. In the nervous system, mkuz mutant embryos show ectopic neuronal differentiation. In the paraxial mesoderm, mkuz mutant embryos show delayed and uncoordinated segmentation of the somites. These phenotypes are similar to those of mice lacking Notch-1 or components of the Notch pathway such as RBP-Jk (Conlon et al, 1995, Development 121, 1533–1545; Oka et al., 1995), indicating a conserved role for mkuz in modulating Notch signaling in mouse development. Furthermore, we detect no visible defect in Notch processing in our knockout animals. Besides the neurogenesis and somitogenesis defect, mkuz mutant mice also show severe defects in the yolk sac vasculature, with an enlarged and disordered capillary plexus and the absence of large vitelline vessels. Since such phenotype has not been observed in mice lacking Notch-1 or RBP-Jk (Swiatek et al., 1994 Genes Dev 15, 707–719; Conlon et al, 1995; Oka et al., 1995 Development 121, 3291–3301), we determine that this phenotype reveals a novel function of mkuz that is distinct from its role in modulating Notch signaling. Taken together, our studies reveal the essential role for an ADAM family disintegrin metalloprotease in mammalian neurogenesis, somitogenesis and angiogenesis.

SUMMARY OF THE INVENTION

We disclosed that Kuz is involved in somitogenesis, neurogenesis and angiogenesis and provides a useful therapeutic target for intervention in associated pathologies. Accordingly, the invention provides methods and compositions relating to Kuz involvement in somitogenesis, neurogenesis, and particularly, angiogenesis. In one embodiment, the invention provides methods for modulating angiogenesis comprising the step of specifically modulating the activity of Kuz in a vertebrate animal predetermined to have a pathogenic angiogenesis. A wide variety of methods for specifically modulating Kuz activity are disclosed, including contacting the animal with an agent which specifically binds the Kuz or competes with the Kuz for substrate or a required cofactor.

In another embodiment, the invention provides methods for modulating angiogenesis comprising the steps of specifically modulating the activity of Kuz in a vertebrate animal not necessarily predetermined to have a pathogenic angiogenesis, but rather subsequently detecting a resultant angiogenic modulation in the animal.

The invention also provides methods for specifically detecting Kuz activity in a vertebrate animal predetermined to have a pathogenic angiogenesis; for example, using a KUZ specific protease assay or a KUZ specific immunobinding assay. The invention also provides methods for specifically detecting a pathogenic angiogenesis in a vertebrate animal having a predetermined Kuz activity; for example, by detecting a tumor associated with pathogenic angiogenesis.

The invention also provides methods for identifying a modulator of angiogenesis, comprising the steps of (a) contacting an angiogenic assay system comprising a predetermined amount of Kuz with a candidate agent, under conditions whereby but for the presence of the agent, the system provides a reference angiogenesis; and (b) detecting an agent-biased angiogenesis of the system; wherein a difference between the agent-biased angiogenesis and the reference angiogenesis indicates that the agent modulates angiogenesis in the system. Such methods may be embodied in an in vitro, cell based assay or an in vivo, animal-based assay.

The invention also provides kits and reagents adapted to the subject methods.

DESCRIPTION OF SPECIFIC EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or. Kuz refers to an art-recognized family of natural proteins which have been extensively described, encompassing natural orthologs and variants also well known in the art. For example, several forms of human KUZ have been described including WO98/37092 and WO97/31931; Mayer et al. (U.S. Pat. No. 5,922,546); and Rubin et al. (U.S. Pat.

No. 5,935,792). Though often discussed and exemplified in terms of angiogenesis, the disclosed methods and reagents are to be understood to be generally applicable to pathogenic somitogenesis and neurogenesis as well.

Several disclosed applications involve specifically modulating the activity of Kuz in a vertebrate animal. A wide variety of methods for specifically modulating Kuz activity are disclosed, including contacting the animal with an agent which specifically binds the Kuz or competes with the Kuz for substrate or a required cofactor.

Agents which specifically bind kuz include metalloprotease inhibitors, such as hydroxamate metalloprotease inhibitors and TACE (TNF-alpha converting enzyme) inhibitors (for review, see Amour A, et al. Ann N Y Acad Sci 1999 Jun 30;878:728–31). Exemplary inhibitors include IC-3 (N-{D,L-[2-(hydroxyaminocaronyl)mehyl]-4-methyl-pentanoyl}-L-alanine, 2-aminoethyl amide, Black et al., Nature, 1997, Vol 385, 729-73; Galko and Tessier-Lavigne, Science, 2000, Vol 289, 1365–1367), GM6001 (NHOHCOCH$_2$CH(I-Bu)CO-Trp-NHMe); GW9471 (see structure of GW9277, a biotinylated derivative of GW9471 used during the purification of TACE as shown in Moss et al, Nature, 1997, Vol 385, 733–736); and BB-94 (batimastat), a synthetic hydroxamate peptidomimetic matrix metalloproteinase inhibitor, see Hemandez-Pando R, et al. Int J Exp Pathol June;2000; 81(3):199–209. Useful natural MMP inhibitors include the tissue inhibitors of MMPs (TIMPs), such as TIMP-1 and TIMP-3 (see, e.g. Amour et al., FEBS Lett. May 2000 19;473(3):275–9).

Another class of inhibitors which specifically bind Kuz are polypeptides comprising immunoglobulin complementary determining regions (CDRs), particularly CDR3 regions which specifically bind Kuz. These encompass antibodies and antibody fragments such as F(ab) fragments. Methods for making and using therapeutic antibodies and antibody fragments are well known, e.g. U.S. Pat. No. 5,935,792.

Intracellular antibodies, or intrabodies, represent a class of neutralizing molecules with applications in gene therapy (vonMehren M,Weiner L M. (1996) Current Opinion in Oncology. 8: 493–498, Marasco Wash. (1997) Gene Therapy. 4: 11–15, Rondon I J, Marasco Wash. (1997) Annual Review of Microbiology. 51: 257–283). Anti-Kuz intrabodies are engineered single-chain antibodies in which the variable domain of the heavy chain is joined to the variable domain of the light chain through a peptide linker, preserving the affinity of the parent Kuz antibody (Rondon et al.). The anti-Kuz intrabodies are designed from either the polyclonal or monoclonal anti-Kuz antibody cDNA that encode antibodies that recognize the enzymatically active form of Kuz and which, upon binding, inhibit Kuz's ability to transphosphorylate. Also, anti-Kuz intrabodies can be made from either polyclonal or monoclonal antibody cDNA that encodes an antibody that stimulates Kuz enzymatic activity. The anti-Kuz single chain intrabodies may be additionally modified with a C-terminal human C kappa domain to increase cytoplasmic stability and/or the C-terminal SV40 nuclear localization signal to direct the nascent intrabody to the nuclear compartment, respectively (Mhashilkar AM, et al. (1995) Embo Journal. 14: 1542–1551). In this regard, stably expressed single chain anti-Kuz intrabodies, and their modified forms, can be used to effectively target Kuz molecules either in the cytoplasm or nuclear compartments of eukaryotic cells.

The Kuz-specific intrabodies can be introduced into cultured cells by any one of several established methods that include the standard DNA transfection methods (Calcium phosphate, electrophoration, lipofectamine, etc.). The anti-Kuz intrabodies are first constructed into any one of a variety of inducible expression vectors tet repressible (Gossen M,Bujard H. (1992) Proc. Natl. Acad. Sci. USA. 89: 5547–5551) or IPTG inducible (Liu HS, et al. (1998) Biotechniques. 24: 624–632, Hannan G N, et al. (1993) Gene. 130: 233–239) or glucocorticoid inducible (using a GRE), constitutive expression vectors (such as CMV or RSV promoter driven vectors ) or tissue specific expression vectors using promoters of tissue specific expressed genes (such as the T cell receptor promoter). A key variation to express the anti-Kuz intrabodies tissues (as well as cell lines) is to construct appropriate viral expression vectors using standard protocols (Vile R G, et al.(1995) British Medical Bulletin. 51: 12–30, Shoji I, et al. (1997) J General Virology. 78: 2657–2664, Paulus W, et al (1996) J Virology. 70: 62–67). The anti-Kuz intrabody genes are substituted for the key viral genes and packaged into a viral particle by a host cell. The altered viral genome is integrated into the target tissue genome but is disrupted in a way that prevents the formation of new viral particles. Individual cells of the target tissues then produce the anti-Kuz intrabody transcripts and proteins.

A wide variety of agents may be used to specifically compete with Kuz for substrate or cofactors. Competitive inhibitors encompass numerous classes, including substituted hydroxamates, carboxylates, thiols, phosphonates, aminodiathiazols, and catechols which are know to inhibit Zn-metalloproteases through high-affinity zinc binding, and chelators of divalent cations, such as EDTA and 1,10-phenanthroline. Competitive inhibitors also include dominant negative Kuz mutants, wherein the protease domain is disrupted by deletion or point mutagenesis. Such Kuz mutants are known in the art and novel dominant negative mutants are readily made by targeted mutagenesis of residues within the protease domain followed by routine activity screening, see U.S. Pat. No. 5,935,792. Exemplary dominant negative human kuz mutants are shown in Table 1.

TABLE 1

Exemplary dominant negative human kuz mutants

| Name | mutation | Dominant Negative Activity |
| --- | --- | --- |
| hKUZDN1 | Δ212–455* | +++ |
| hKUZDN2 | Δ213–381 | +++ |
| hKUZDN3 | Δ382–392 | +++ |
| hKUZDN4 | Δ382–392 & Δ677–748 | +++ |
| hKUZDN5 | E384 to A | +++ |
| hKUZDN6 | E384 to A & Δ675–748 | +++ |
| hKUZDN7 | S391 to A | +++ |
| hKUZDN8 | AHE384–386 to AAA | +++ |

"Numbering" refers to the amino acid residues as set forth in the human Kuz (SEQ ID NO:4) of U.S. Pat. No. 5,935, 792. Corresponding mutations can be identified in other human Kuz proteins, such as disclosed in U.S. Pat. No. 5,922,546 and PCT publication WO 97/31931, by sequence alignment.

In a preferred embodiment, the dominant negative Kuz mutant is soluble, i.e. lacking the transmembrane domain but comprising one or more of the extracellular domains. Preferably, the soluble dominant negative mutant also lacks the signal peptide and prodomain, and comprises the cysteine-rich domain, the disintegrin domain and/or the metalloprotease domain. In another preferred embodiment, the soluble dominant negative mutant is fused to an unrelated polypeptide selected to facilitate purification, detection, or solubilization, or to provide some other function. Fusion proteins are generally produced by expressing a hybrid gene in which a nucleotide sequence encoding the soluble Kuz mutant joined in-frame to a nucleotide sequence encoding the selected unrelated polypeptide. A preferred unrelated protein is the constant (Fc) region of an immunoglobulin (e.g. a human IgG Fc region), which can render the resulting fusion protein more stable and with a longer half-life when used as a biotherapeutic.

Several disclosed applications involve a vertebrate animal, particularly a mouse, rat or human, which has been predetermined to have pathogenic somitogenesis, neurogenesis or particularly, angiogenesis. In other embodiments, the methods involve specifically detecting the pathogenic angiogenesis, somitogenesis or neurogenesis in the animal. Pathogenic angiogenesis for example, encompasses any condition presenting undesirably excessive or deficient angiogenesis, systemically or regionally; exemplary underlying conditions include cancer, diabetic retinopathy, rheumatoid arthritis, macular degeneration, psoriasis and other pathologies in which excessive, insufficient or misregulated angiogenesis plays a role. For example, our Kuz-deficient mice present upregulation of several neural specific genes, including Mash-1 and neurogenin, indicating an excess of neural precursors. These mice also present defective somitogenesis as revealed by loss of Dl11 expression in somites and severe phenotypic disruption of the somites. In addition, the mice present pathogenic angiogenesis, wherein vitelline vessels in the embryonic yolk sack fail to develop. The pathogenic somitogenesis, neurogenesis or angiogenesis are readily detected by routine methods, such as histological exam, expression of correlating marker genes, etc. In addition, numerous in vitro model systems are known, such as endothelial cell based angiogenesis assays, as exemplified below. In many cases, detection is effected inferentially by detecting a condition, such as a tumor, which is associated with a pathogenic angiogenesis. Angiogenesis in particular is detected by any convenient means, including in vitro, cell-based assays such as huvec assays and in vivo measures such as blood flow paramenters, microvessel density, vascular endothelial growth factor levels (see, e.g. Lee et al. Obstet Gyneco October;2000 96(4):615–21), growth factor receptors (e.g. Shin et al. 2000 J Cancer Rec Clin Oncol 126, 519–28. etc., These assays may be practiced in model systems, such as heterologous transplant systems, e.g. Rofstad et al. 2000 Cancer Res 60, 4932–8.

The present disclosure that Kuz provides a useful therapeutic target for conditions associated with pathogenic somitogenesis, neurogenesis or angiogenesis provides numerous applications that will be apparent to those skilled in the art—any application premised on the used of Kuz as a therapeutic target for conditions associated with pathogenic somitogenesis, neurogenesis or angiogenesis. For example, in one embodiment, the invention provides methods for modulating angiogenesis comprising the steps of specifically modulating the activity of Kuz in a vertebrate animal not necessarily predetermined to have a pathogenic angiogenesis, but rather subsequently detecting a resultant angiogenic modulation in the animal. In another embodiment, the invention also provides methods for specifically detecting Kuz activity in a vertebrate animal predetermined to have a pathogenic angiogenesis; for example, using a KUZ specific protease assay or a KUZ specific immunobinding assay. In another embodiment, the invention provides methods for specifically detecting a pathogenic angiogenesis in a vertebrate animal having a predetermined Kuz activity; for example, by detecting a tumor associated with pathogenic angiogenesis.

The invention also provides methods for identifying a modulator of angiogenesis which is a priori known to be associated with Kuz activity. An exemplary such method comprises the steps of (a) contacting an angiogenic assay system comprising a predetermined amount of Kuz with a candidate agent, under conditions whereby but for the presence of the agent, the system provides a reference angiogenesis; and (b) detecting an agent-biased angiogenesis of the system; wherein a difference between the agent-biased angiogenesis and the reference angiogenesis indicates that the agent modulates angiogenesis in the system. Such screening methods may be embodied in an in vitro, cell based assay or an in vivo, animal-based assays, such as described below.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All publications and patent applications cited in this specification are herein incorporated by reference as if each individual publication or patent application were specifically and individually indicated to be incorporated by reference.

EXAMPLES

1. Vascular Endothelial Growth Factor, Interleukin 8, Platelet-derived Endothelial Cell Growth Factor, Basic Fibroblast Growth Factor and Kuz Promote Angiogenesis and Metastasis in Human Melanoma Xenografts This study demonstrates that angiogenesis and metastasis of melanoma are inhibited by inhibitors of several known angiogenic factors, including Kuz. Experimental details are adapted from Rofstad, et al. 2000 Cancer Res 60, 4932–8. Briefly, cells from human melanoma lines (A-07, D-12, R-18, and U-25) transplanted to BALB/c nu/nu mice are used as tumor models. Expression of angiogenic factors is studied by ELISA, Western blotting, and immunohistochemistry. Angiogenesis is assessed by using an intradermal angiogenesis assay. Lung colonization and spontaneous lung metastasis are determined after i.v. and intradermal inoculation of tumor cells, respectively. The specific role of VEGF, IL-8, PD-ECGF, bFGF and Kuz in tumor angiogenesis, lung colonization, and spontaneous metastasis are assessed in mice treated with neutralizing antibody or dominant negative mutants. The melanoma lines express multiple angiogenic factors and each line shows a unique expression pattern. Multiple angiogenic factors promote angiogenesis in the most angiogenic melanoma lines. Tumor growth, lung colonization, and spontaneous metastasis are controlled by the rate of angiogenesis and hence by the angiogenic factors promoting the angiogenesis. Lung colonization and spontaneous metastasis are inhibited by treatment with neutralizing antibody or dominant negative mutants. Results demonstrate that each of the subject angiogenic factors can promote angiogenesis and metastasis in human melanoma xenografts and each provides a validated target for therapeutic intervention.

Methods: Adult (8–10 weeks of age) female BALB/c nu/nu mice are used to assess tumor angiogenesis, lung colonization, and spontaneous metastasis.

Four human melanoma cell lines (A-07, D-12, R-18, and U-25, Rofstad,.Br. J. Cancer, 70: 804–812, 1994) are maintained in monolayer culture in RPMI 1640 (25 mM HEPES and L-glutamine) supplemented with 13% bovine calf serum, 250 mg/l penicillin, and 50 mg/l 30 streptomycin. The cultures are incubated at 37° C. in a humidified atmosphere of 5% $Co_2$ in air and subcultured twice a week. The cell lines are verified to be free from Mycoplasma contamination.

Tumor angiogenesis is assessed by using an intradermal angiogenesis assay (Danielsen, T. et al., Int. J. Cancer, 76: 836-841, 1998). A 100-µl Hamilton syringe is used to inoculate aliquots of 10 µl of cell suspension into the flanks of mice. The inoculation point lies above the S.C. muscle tissue in the deeper part of the dermis. The number of cells per inoculum is $1.0 \times 10^6$. The mice are killed on day 7 after the inoculation—small vascularized tumors develop in the inoculation sites by that time. The skin around the inoculation sites is removed, and the tumors located with a dissecting microscope. The capillaries in the dermis oriented toward the tumors are counted, and the diameters of the tumors measured, using an ocular with a scale. The number of capillaries is corrected for the background, determined after the injection of 10 µl of HBSS. Angiogenesis is quantified as a number of capillaries per tumor or number of capillaries per mm of tumor circumference.

Treatment with Neutralizing Antibody in Vivo. The specific roles of VEGF, IL-8, PC-ECGF, bFGF and Kuz in tumor angiogenesis, lung colonization, and spontaneous metastasis are investigated by treating host mice with neutralizing antibody against these angiogenic factors. The antibodies used for treatment are antihuman VEGF mouse monoclonal antibody, antihuman IL-8 mouse monoclonal antibody, antihuman PD-ECGF goat polyclonal antibody, antihuman bFGF goat polyclonal antibody and antihuman Kuz antibody. The antibody solutions are diluted in PBS and administered to the mice in volumes of 0.25 ml by i.p. injection. In the angiogenesis and lung colonization experiments, the treatments consist of four doses of 25 µg (VEGF and bFGF) or 100 µg (IL-8 and PD-ECGF) of antibody given in intervals of 24 h. The first dose is given lh before the tumor cell inoculation.

Treatment with Neutralizing Antibody in Vitro. Possible cytotoxic or antiproliferative effect of the neutralizing antibodies described above are investigated in vitro. A-07, D-12, R-18 or U-25 cells are cultured in RPMI 1640 (25 mM HEPES and L-glutamine) supplemented with 13% bovine calf serum, 250 mg/l penicillin, and 50 mg/l streptomycin in the absence or presence of 5 µg/ml of antibody for up to 8 days. The number of cells in the cultures is determined 2, 4, 6, or 8 days after the cultures are initiated by counting cells in a hemocytometer.

2. Inhibition of Angiogenesis by Kuz Inhibitors

In this example, Kuz inhibitors including IC-3, GM6001, GW9471, BB-94, TIMP-1 and 2 are shown to inhibit angiogenesis in several model systems. The presence of Kuz and its activity is assayed by ELISA and Kuz-specific protease activity prior to or subsequent to the measure of angiogenesis. Our results demonstrate that the Kuz inhibitors reduce tube formation by rat microvascular endothelial cells plated on matrigel and significantly reduce bFGF (10 ng/ml)+TNFalpha (2.5 ng/ml)-stimulated microvessel formation by human microvascular endothelial cells plated on fibrin by 30–70%. Furthermore, inhibitor concentration dependently inhibited spontaneous microvessel formation in the rat aorta-ring assay and vessel development in the chick chorioallantoic membrane assay.

The methods were adapted from Manolopoulos VG, et al. Gen Pharmacol Febuary;2000 34(2): 107-16. Microvascular endothelial cells from the rat adrenal medulla (RAMECs) are isolated, grown, and characterized (Manolopoulos, et al., 1997 Biochim Biophys Acta 1356, 321–332; Manolopoulos, et al., 1997 Am J. Physiol. 273, C214–C222.) The cells are cultured in DMEM supplemented with 10% $CO^2$ in air, and used at passages 17–19. Human foreskin microvascular endothelial cells (HMVECs) are isolated and grown as previously described (Koolwijk, et al. 1996. J. Cell Biol. 132, 1177–1188. ). The cells are cultured in gelatin-coated dishes in M199 supplemented with 20 mM HEPES (pH 7.3), 10% human serum, 10% newborn calf serum (NBCS), 150 µg/ml ECGF, 5 IU/ml heparin, 2mM L-glutamine, and antibiotics, at 37° C., 5% $CO_2$ in air, and used at passage 10 or 11. Both cell types are passaged by brief exposure to 0.5 g/l trypsin-EDTA in a $Ca^{2+}/Mg^{2+}$-free solution.

The matrigel assay is performed according to Kubota Y. et al., 1988. J. Cell Biol. 107, 1589–1598. Matrigel, a tumor extract containing basement-membrane components at 15.8 mg/ml, is applied to 1-$cm^2$ wells (120 µl/well) and allowed to solidify at 37° C. for 1 h. Subsequently, 50,000 RAMECs are seeded in each well and incubated with complete DMEM containing the drugs under study at 37° C. for 8 h. The incubation period chosen (8 h) is found in preliminary studies to be the minimal necessary for optimal tube formation under our experimental conditions. The total length of the tubular structures formed in each well is measured in six microscopic fields (at 2.5×magnification) covering the entire well surface by using a microscope equipped with a video camera connected to a computer with OPTIMAS image analysis software (Tokyo, Japan).

The fibrin gel assay is performed as described by Koolwijk, et al. supra. Briefly, human fibrin matrices are prepared by the addition of 0.1 U/ml thrombin to a mixture of 2.5 U factor XIII, 2 mg human fibrinogen, 2 mg Na citrate, 0.8 mg NaCl, and 3 µg plasminogen per milliliter of M199 medium without indicator. A total of 300 ml of this mixture is added to 1-$cm^2$ wells. After clotting at room temperature, fibrin matrices are soaked with 0.5 ml M199 supplemented with 10% human serum, 10% NBCS, and antibiotics. Endothelial cells are seeded at high density to obtain confluent monolayers and are cultured in M199 medium without indicator supplemented with 20 mM HEPES (pH 7.3), 10% human serum, 10% NBCS, 2 mM L-glutamine, antibiotics, 10 ng/ml bFGF, and 2.5 ng/ml TNFα. Incubations are allowed to proceed for 10 days, with fresh medium and test compounds being added every 2 to 3 days. The tubular structures formed by endothelial cells in the three-dimensional fibrin matrix are observed by phase-contrast microscopy, and their total length in each well is measured in six microscopic fields covering the entire well surface by using an Olympus microscope equipped with a monochrome CCD camera (MX5) connected to a computer with OPTIMAS image analysis software.

The rat aorta-ring assay of angiogenesis is performed as described by Liekens, et al., 1997 Oncol. Res. 9, 173–181. Briefly, a sterile 1.5% solution of agarose is poured into culture dishes and allowed to gel. Agarose rings are obtained by punching two concentric circles, with diameters of 10 and 17 mm, respectively, in the agarose gel. The rings are transferred to six-well plates, three rings in each well. Thoracic aortas are obtained from adult male Wistar rats, cleaned from fat and connective tissue, and sectioned in 0.5-mm rings. Each aortic ring is positioned at the center of an agarose well, the bottom of which has already been coated with 150 µl of clotting fibrinogen, and then the agarose well is completely filled with clotting fibrinogen. The fibrinogen solution used is obtained by dissolving partly purified bovine fibrinogen in serum-free medium to obtain a concentration of 3 mg/ml. The fibrin gel forms within 30 s at room temperature. After fibrin gelation, each well is filled with M199 medium supplemented with 20% FCS, 10 mM HEPES, 1 mM glutamine, and antibiotics, and the test compounds are added. Cultures are examined daily and scored under an inverted microscope. Formation of more than 200 microvessels is common, owing to the three-dimensional complexity of the microvascular network; therefore, the formed microvessels are scored on a scale from 0 (no vessels) to 10 (maximum vessel number) by two independent observers.

The chorioallantoic membrane vessel development assay is performed as described by Liekens et al, supra. Briefly, fresh fertilized eggs are incubated at 37° C. (humidity 55–60%) for 4 days before a window is opened on the eggshell, exposing the CAM. The window is covered with cellophane tape, and the eggs are returned to the incubator. On day 9, plastic discs (10-mm diameter), on which the test compounds have been allowed to dry under sterile conditions, are applied to selected areas of the CAM, one disc in each CAM. In addition, a control disc (containing PBS or DMSO) is placed on each CAM, 1 cm away from the disc containing the test compounds. A sterile solution of cortisone acetate (100 µg/disc) is incorporated in all discs to prevent an inflammatory response. Thereafter, the windows are covered, and the eggs are incubated at 37° C. for 48 h. Incubation is terminated by flooding of the eggs with 10% buffered formalin, and the plastic discs are removed.

The eggs are kept at room temperature for at least 4 h, and then a large area around the discs is cut off and placed on a glass slide. The vascular density index under the discs (expressed as number of blood vessels) is measured (Harris-Hooker et al., 1983. J. Cell Physiol.114, 302–310). Briefly, membranes are fixed in 10% buffered formalin, excised, and laid flat on a glass slide. The vessel density is determined by covering with a grid the spot where the disc has been. The grid contains three concentric circles (1 mm apart) that covers the area of interest. The vessels intersecting the circles are counted. This method allows for an objective evaluation of microvessel formation, taking into account the small, recently formed microvessels. Overall chick embryo survival until disc implantation is over 90%. Control discs receive the same volume of DMSO as the discs containing the compounds.

3. Kuz Promotes Formation of Vascular Structures in Vitro

The formation of vascular-like structures by HUVEC is assessed on the basement membrane matrix preparation, growth factor-reduced Matrigel (Becton Dickinson, Bedford, Mass.), as described in Kureishi Y, et al. Nat Med September;2000 6(9):1004–10. Two-well chamber slides are coated with Matrigel (10 mg/ml) according to the manufacturer's instructions. HUVEC are seeded on coated plates at $4$–$5 \times 10^4$ cells/well in EBM and incubated at 37 O° C. for 60 minutes. The media are supplemented with the agents (metalloprotease domain of human Kuz, Kuz inhibitors, Kuz antibodies, VEGF, etc.) and incubated at 37° C. for 8–12 h. Tube formation image is observed using an inverted phase contrast microscope (Nikon Diaphot). Images are captured with a video graphic system (DEI-750 CE Digital Output Camera, Optronics, Goleta, Calif.). The degree of tube formation is quantified by measuring the length of tubes in random fields from each well using the National Institutes of Health (NIH) Image Program. Like VEGF, Kuz treatment promotes the formation of capillary-like tubes, which is inhibited by Kuz inhibitors and antibodies.

4. Kuz Promotes Angiogenesis in Normocholesterolemic Animals: Limb Revascularization Here we show that Kuz promotes and Kuz inhibitors can reduce physiological revascularization of ischemic tissue. In a protocol adapted form Kureishi Y, et al. Nat Med September;2000 6(9):1004–10, normocholesterolemic rabbits are subject to unilateral resection of their femoral arteries and their main branches, resulting in a marked decrease in hindlimb perfusion (Pu, et al. J Surg Res. 54, 575–583, 1993). Initially, we use adenovirus-mediated gene transfer to endothelial cells of the ischemic hindlimb to first demonstrate that Kuz promotes angiogenesis in this model. Infusion of these limbs with an adenovirus construct expressing B-galactosidase (Bgal) revealed that transgene expression was restricted to the vascular endothelium. Infusion of a adeno-Kuz constructs in this model enhances collateral vessel formation, and improves tissue perfusion as indicated by an increase in calf blood pressure ratio. In contrast, infusion with adeno-Bgal did not promote vessel formation or tissue perfusion relative to untreated ischemic hindlimbs (control) or vessels infused with saline.

To test the effects of Kuz and Kuz inhibitors on limb revascularization, Kuz and inhibitor dosages are administered daily (e.g. 0.1 mg/kg IC-3 by intraperitoneal injection) after femoral artery resection. Animals receiving Kuz treatment display more detectable collateral vessels with characteristic corkscrew morphology than the untreated control group at 40 days following femoral artery resection. In contrast, animals receiving Kuz inhibitor treatment display less detectable collateral vessels with characteristic corkscrew morphology than the untreated control group at 40 days following femoral artery resection.

Correspondingly, the limbs of the Kuz-treated animals display reduced hemodynamic deficit determined by ratio of the systolic pressure of the ischemic limb to that of the normal limb. Kuz administration also promotes capillary formation in the ischemic limb (Kuz>250 capillaries/mm$^2$; control<170 capillaries/mm$^2$ in adductor muscle; P<0.01). For comparison, some animals receive an intramuscular injection of an adenovirus encoding VEGF (adeno-VEGF) into the thigh of the ischemic limb. Like Kuz, VEGF treatment enhanced collateral and capillary vessel formation and increased calf blood pressure. Coadministration of Kuz inhibitors are shown to reverse these effects.

Methods: Male New Zealand white rabbits, weighing 3.0–3.5 kg and fed a normal diet, are used to examine the effects of Kuz and Kuz inhibitor-mediated modulation of vessel growth. For the infusion model, the left femoral artery and main side branches are excised from their proximal origin to within 2 cm of the bifurcation into the saphenous and popliteal arteries. After 10 days, to permit post-operative recovery, the distal femoral artery is re-exposed and, after temporary clamping of the femoral vein, 50 ml of saline, saline with $3.5 \times 10^{10}$ viral particles of Ad-Bgal, or saline with $3.5 \times 10^{10}$ viral particles of Ad-Kuz (expressing metalloprotease domain of human Kuz) is infused through the distal femoral artery and incubated for 15 min. After clamp removal, the distal femoral artery is ligated. Two animals infused with Ad-Bgal are killed 3 days after surgery to determine B-galactosidase expression in the gastrocnemial muscle. The remainder of the animals (n=6) are analyzed for limb revascularization at 31 days after femoral artery resection. For the intramuscular injection of Ad-VEGF or the intraperitoneal injection of Kuz inhibitor, the left femoral artery and side branches are completely excised from their proximal origin to the point distally where bifurcation occurs. After 10 days, to permit post-operative recovery, a total of $3.5 \times 10^{10}$ viral particles of Ad-VEGF in 2.5 ml of saline is injected through a 27-gauge needle at a depth of 3 to 5 mm in the adductor (2 sites), medial large (2 sites) and semimembranous (1 site) muscle (500 ul per injection site). Alternatively, inhibitor (IC-3, 0.1 mg/kg/day) or saline is given intraperitoneally (1 ml) from the day after surgery until one day before sacrifice. Animals in these groups (n=6) are analyzed for limb revascularization 40 days after surgery. No adverse events, including death, edema or angioma formation, are noted with any treatment regimen. Calf blood pressure is measured in both limbs by Doppler flow meter (model 1059, Parks Medical Electronics, Aloha, Oreg.). The calf blood pressure is defined as the ratio of the left calf to right calf systolic pressure. Collateral arteries are evaluated by internal iliac angiography. A 3-F infusion catheter (Tracker-18, Target Therapeutic, San Jose, Calif.) is introduced into the common carotid artery and advanced to the internal iliac artery of the ischemic limb using a 0.014-inch guide wire under fluoroscopic guidance. Non-ionic contrast media (Isovue-370, Squibb Diagnostics, New Brunswick, N.J.) is injected at a rate of 1 ml/sec and serial images of the ischemic hindlimb are recorded at a rate of 1 film/sec for 10 sec. Quantitative angiographic analysis of collateral vessels are performed by an investigator blinded to the outcome using a grid overlay composed of 2.5-mm diameter circles arranged in rows spaced 5 mm apart placed over the 4-sec angiogram. An angiographic score is calculated as the number of circles crossed by visible arteries divided by the total number of circles in the medial thigh. Capillary density is evaluated by investigator blinded to the outcome using light microscopic sections taken from the adductor muscle of the ischemic limb at the time of euthanasia. Muscle samples are embedded in OCT compound (Miles, Elkhart, Ind.) and snap-frozen in liquid nitrogen. Frozen sections (5 um in thickness) with muscle fibers oriented in a transverse fashion are stained for alkaline phosphatase using indoxyl-tetrazolium, and then counterstained with 0.5% eosin. The capillary density is calculated as capillaries/mm$^2$ averaged from 10 randomly selected fields.

5. Kuz Promotes Angiogenesis in Chicken Chorioallantoic Membrane Assay

In a protocol adapted form Bellahcene A, et al. Circ Res April 2000 28;86(8):885–91, fertilized Lohman-selected White Leghorn eggs are incubated at 37° C. in a humidified incubator. On the third day of development, a rectangular window was opened in the egg shell. On day 8, two Silastic rings with an inner diameter of 3.5 mm (height 500 mm, weight 7 mg) are placed on the chick embryo chorioallantoic membrane (CAM) surface. Kuz (human, metalloprotease domain, 15 mM is dissolved in sterile PBS and applied in 5 ml aliquots inside the rings. Vehicle alone (PBS) and a stimulator of blood vessel formation, basic FGF (bFGF, 0.5 mM), are used as negative control and positive controls, respectively. In other experiments, the anti-avb3 antibody LM609 (15 mg) is added to the ring to evaluate its effect on vascular development in presence of Kuz. CAMs were examined daily until day 10 and photographed in ovo under a Leica DMLM microscope (Van Hopplynus, Brussels, Belgium). A minimum of 8 eggs for each condition is treated and the experiments are reproduced at least two times. A vascular index is determined by counting all discernible vessels traversing the ring as described (Barnhill et al. *J Invest Dermatol*. 1983;81 :485–488) and is expressed as the relative increase of the number of vessels in the different experimental conditions compared to the control PBS ring. Our results demonstrate that Kuz stimulates ongoing angiogenesis on the chorioallantoic chick membrane assay. Kuz angiogenic activity was inhibited by Kuz inhibitors, dominant negative mutants and Kuz-specific antibody.

What is claimed is:

1. A method for identifying a modulator of angiogenesis, comprising the steps of contacting an angiogenic assay system comprising an exogenous or predetermined amount of Kuz with a candidate agent, under conditions whereby but for the presence of the agent, the system provides a reference angiogenesis; and detecting an agent-biased angogenesis of the systemn, wherein a difference between the agent-biased angiogenesis and the reference angiogenesis indicates that the agent modulates angiogenesis in the system.

2. A method according to claim 1 wherein the method assesses intradermal angiogenesis in human melanoma xenografts in mice.

3. A method according to claim 1, wherein the method assesses tube formation by rat microvascular endothelial cells plated tumor extract containing basement membrane components.

4. A method according to claim 1, wherein the method assesses microvessel formation by human microvascular endothelial cells plated on fibrin.

5. A method according to claim 1, wherein the method assesses microvessel formation in a rat aorta-ring assay.

6. A method according to claim 1, wherein the method assesses formation of vascular-like structures by HUVEC on a basement membrane matrix preparation, growth factor-reduced tumor extract containing basement membrane components.

7. A method according to claim 1, wherein the method assesses ischemic limb tissue revascularization in normocholesterolemric rabbits.

8. A method according to claim 1, wherein the method assesses angiogenesis in a chicken chonioallantoic membrane assay.

* * * * *

UNITED STATES PATENT AND TRADEMARK OFFICE
CERTIFICATE OF CORRECTION

PATENT NO.  : 6,436,629 B1
DATED       : August 20, 2002
INVENTOR(S) : Pan et al.

It is certified that error appears in the above-identified patent and that said Letters Patent is hereby corrected as shown below:

Column 12,
Line 34, the printer omitted the "on" between "plated" and "tumor".
Line 50, "chonioallantoic" should be -- chorioallantoic --

Signed and Sealed this

Twelfth Day of November, 2002

*Attest:*

*Attesting Officer*

JAMES E. ROGAN
*Director of the United States Patent and Trademark Office*